United States Patent [19]

Mentha et al.

[11] 3,939,181
[45] Feb. 17, 1976

[54] INTERMEDIATES FOR THE PREPARATION OF PYRIMIDINE COMPOUNDS

[75] Inventors: John W. Mentha, Washington; Janice V. Shaffner, Greenville; Ronald M. Cresswell, Raleigh, all of N.C.

[73] Assignee: Burroughs Wellcome Co., N.C.

[22] Filed: Aug. 5, 1974

[21] Appl. No.: 494,721

Related U.S. Application Data

[60] Division of Ser. No. 256,339, May 24, 1972, Pat. No. 3,849,416, which is a continuation-in-part of Ser. No. 177,502, Sept. 2, 1971, abandoned.

[52] U.S. Cl. ... 260/340.7; 260/256.4 N; 260/340.3; 260/340.5; 260/340.9; 260/465 R; 260/465 G; 424/251
[51] Int. Cl.² ............. C07D 317/30; C07D 319/06; C07D 321/04
[58] Field of Search ............. 260/338, 340.3, 340.5, 260/340.7, 340.9

[56] References Cited
UNITED STATES PATENTS

| | | | |
|---|---|---|---|
| 3,072,679 | 1/1963 | Batzer et al. | 260/340.7 |
| 3,454,596 | 7/1969 | Hamilton | 260/340.7 X |

*Primary Examiner*—Richard L. Raymond
*Attorney, Agent, or Firm*—Donald Brown

[57] ABSTRACT

There is disclosed a method of making compounds represented by the formula

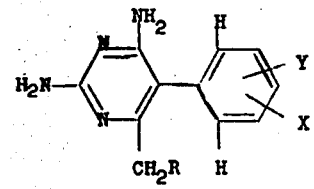

and which are useful as antimalarial agents. The method includes reacting a keto nitrile with a polyhydroxy compound and then reacting the product with guanidine base. In the above X is a halogen atom or a nitro group, Y is a halogen atom or hydrogen and R is hydrogen or alkyl containing 1 to 10 and preferably is lower alkyl containing 1 to 4 carbon atoms.

18 Claims, No Drawings

INTERMEDIATES FOR THE PREPARATION OF PYRIMIDINE COMPOUNDS

This is a division of application Ser. No. 256,339 filed on May 24, 1972, now U.S. Pat. No. 3,849,416 which is a continuation-in-part of application Ser. No. 177,502 filed Sept. 2, 1971, now abandoned.

BACKGROUND OF THE DISCLOSURE

This disclosure is directed to a new and improved method of making 2,4-diamino-5-phenyl-6-alkyl pyrimidines and new intermediates useful in the preparation thereof.

Reference may be had to U.S. Pat. No. 2,576,939 as well as British Journal of Pharmacology and Chemotheraphy, June, 1951, Vol. 6, No. 2, p. 185 for the article entitled 2, 4-Diamino Pyrimidines - A New Series of AntiMalarials by E. A. Palco et al., for a discussion and disclosure of antimalarial compounds of the type which may be synthesized by the methods disclosed herein.

In particular, this invention is directed to a new and improved method for making antimalarial compounds of formula I

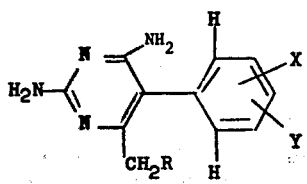

where X is a halogen atom (chlorine, iodine, fluorine, or bromine) or a nitro group, Y is a halogen group (chlorine, iodine, fluorine, or bromine) or hydrogen where X is halogen (chlorine, iodine, fluorine, or bromine) or nitro and R is hydrogen or lower alkyl containing 1 to 4 carbon atoms (methyl, ethyl, propyl or butyl).

The compounds of formula I or IA are useful as antimalarial agents and may be administered orally in a conventional manner, e.g., tablets to humans (adults or children) at a dosage of 25 mg. weekly and at a dosage of 12.5 mg. weekly for children.

Of the compounds of formula I or IA, the compound 2,4-diamino-5-p-chlorophenyl-6-ethyl pyrimidine (pyrimethamine) has proved most successful in treating malaria infections in man and has been widely used for this purpose.

In the past, the compounds of formula I or IA have been primarily prepared by the methods disclosed in U.S. Pat. Nos. 2,602,794 and 2,576,939. Although the process of U.S. Pat. No. 2,602,794 have proven to be quite useful in practice, particularly in small scale operations, it has been difficult to date to maintain high yields in making the required intermediates as the process disclosed therein is scaled up for large scale manufacturing operations.

Unexpectedly, it has now been found that with the process of the present invention it is possible to scale up manufacture without experiencing large reductions in yield of the new intermediates compared with the yields obtainable under laboratory conditions.

Accordingly, this invention provides a new and improved process for preparing the compounds of formula I or IA much more economically than heretofore possible. The above has been accomplished by providing new and improved methods for preparing new and unobvious intermediates which are then further reacted with guanidine base to provide the compounds of formula I or IA.

BRIEF DESCRIPTION OF THE DISCLOSURE

The process of the present invention comprises the reaction of a keto nitrile according to the formula II or formula IIA

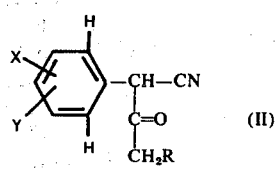

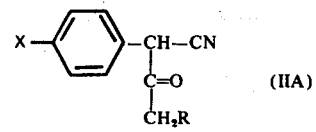

and R is hydrogen or alkyl containing 1 to 10 carbon atoms and more preferably lower alkyl containing 1 to 4 carbon atoms (methyl, ethyl, propyl, or butyl) and more preferably for making the antimalarial compounds of formula IA

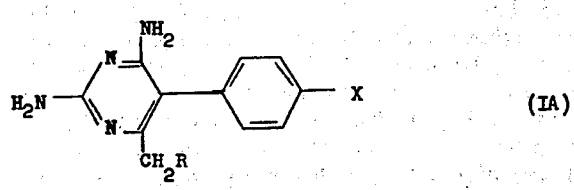

where X is halogen atom (chlorine, iodine, fluorine or bromine) or a nitro group, Y is a halogen atom (chlorine, iodine, fluorine or bromine) or hydrogen and R is alkyl of 1 to 10 carbon atoms and is preferably lower alkyl of 1 to 4 carbon atoms, or hydrogen (where X is chlorine and R is methyl when pyrimethamine is being prepared) with a polyhydroxy compound H (OH)$_s$ where $s$ is an integer 2, 3 or greater and M is a hydrocarbon portion of the compound which acts as a carrier for the OH groups and as long as the hydroxyl groups are positioned in the polyhydroxy compound structure so that the compound of formula IV or IV$^1$ is obtained.

Suitable polyhydroxy compounds include polyhydroxy alcohols such as glycol, glycerols including alkyl alcohols and cyclic alkyl alcohols of this type having at least two hydroxyl groups positioned at the 1 and 2 ring position, and is preferably a compound of formula III

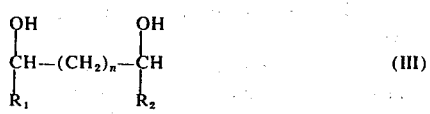

wherein N=0, 1 or 2 and is most preferably 0 or 1 and R₁ or R₂ are the same or different and each is a hydrogen or lower alkyl of 1 to 4 carbon atoms (methyl, ethyl, propyl or butyl) optionally substituted by acid insensitive groups such as hydroxy, halogen (chlorine, bromine, iodine, fluorine), or lower alkoxy of 1 to 4 carbon atoms (methoxyl, ethoxyl, propoxyl, butoxyl) or when n=0,R₁ and R₂ can complete a 5 to 7 member saturated ring, capable of reacting with a compound of the formula II or IIA to prepare the corresponding cyclic ketal intermediates having the general formula IV or IV¹

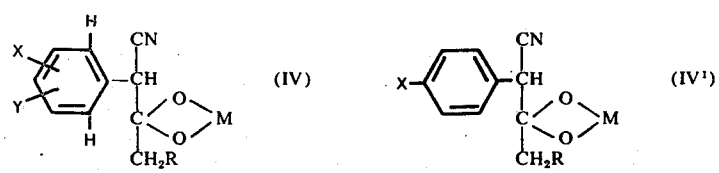

where M is defined as above and can represent the portion of a molecule such as a polyhydroxy alcohol molecule used in the reaction as the starting material and which is essentially inert and acts as a carrier for the polyhydroxy groups attached thereto, and X, Y and R are defined as above, and when the preferred compound of formula III is reacted the compounds of formula IVA and IVA¹ are obtained.

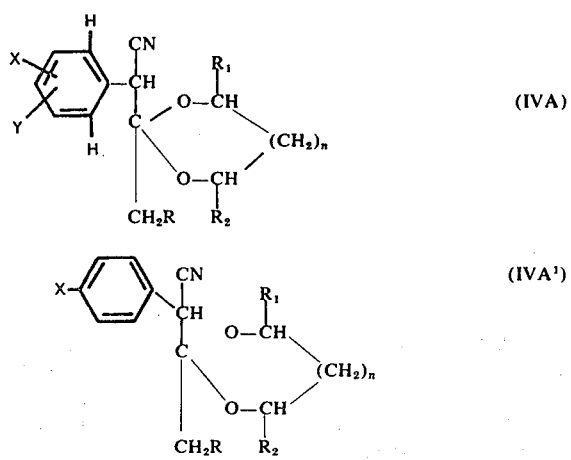

In formulas IVA and IVA¹, X, Y, R, R₁, R₂ and n are as defined above and where pyrimethamine is prepared X is Cl and R is methyl in formula IVA¹.

Most preferably the alcohols used are 1, 2-ethanediol, 1,2-propanediol, and 1, 3-propanediol to achieve outstanding yields. The reaction preferably takes place in a solvent, most preferably one that will allow the azeotropic removal of water [since water is produced in the reaction] at a resonable high reaction temperature. Suitable solvents include benzene, toluene, xylene, butyronitrile and dibutyl ether all of which are immiscible with water. It should be understood obviously that the exact nature of the solvent is not critical and that many other solvents not named could be used, although the aforementioned are preferred.

The foregoing reaction is most conveniently carried out at reflux, i.e., the boiling point of the solvent. If azeotropic distillation is used to remove water formed during the reaction reflux is the most preferred temperature. Although reflux temperatures are the most convenient a temperature between 50° to 180°C may be used, with a temperature of 80° to 150°C being preferred and a temperature of 110° to 150°C being most preferred depending necessarily upon the boiling point of the solvent being employed.

The above reaction is one that is catalyzed by the use of an acid catalyst, preferably a strong non-oxidizing acid such as a strong Bronsted Acid (i.e. a proton donor) e.g., hydrocarbyl sulfonic acid or sulfuric acid.

Suitable examples of acids useable in the reaction include p-toluene sulfonic acid, ethansulfonic acid, and sulfuric acid. It is preferable that the amount of acid used in the reaction be between 0.1 to 30% based on the weight of the keto nitrile compound of formula II, and is more preferably betwen 6 to 25% and is most preferably between 10 to 25%. More acid than 30% may be used if desired, but no advantage is achieved and causes additional costs in isolating the produce.

The polyhydroxy alcohol starting materials may be purchased and their methods of preparation are quite conventional. The preferred polyhydroxy alcohols include ethylene glycol, 1,3-propenediol, glycerol although other glycols as for example, 1, 4-butanediol, 2,3-dimethyl-2,3-butanediol, cis-1,2-cyclopentanediol, trans-1,2-cyclohexandiol as well as others may be used.

The keto nitrile starting materials are conveniently prepared as shown in U.S. Pat. Nos. 2,602,794 and 2,576,939 by the reaction of the appropriate benzylhalides with alkali cyanides and then the reaction of the product thereof with the appropriate ester of the formula R CH₂CO₂ R₃ in the presence of an alkali alkoxide where R is as defined above, and R₃ is lower alkyl of 1 to 4 carbon atoms. See in particular Example 3 of U.S. Pat. No. 2,602,794.

In order to prepare the compounds of formula I, the compounds of formula IV, IVA, IV¹ or IVA¹ are condensed with guanidine base in the manner as shown in U.S. Pat. No. 2,602,194.

The guanidine base may be conveniently prepared as an alcoholic solution by mixing guanidine hydrochloride in ethanol with sodium methylate in methanol and filtering. The alcoholic solution of guanidine base is then mixed with the compound of formula IV, IVA, IV¹ or IVA¹ and the methanol is removed as by distillation. Thereafter the reaction mixture is heated, e.g., to reflux and then allowed to cool to give the compound of formula 1 or IA.

Accordingly, in its broadest aspect the invention provides a new and improved method of preparing compounds of formula I or IA.

Yet in another aspect the invention provides a new and improved method for preparing compounds of formulas IV, IVA, IV[1] and IVA[1].

In a further aspect the invention provides new and unobvious intermediate compounds of formulas IV, IV[1], IVA and IVA[1] useful in the preparation of the compounds of formula I or IA.

The following examples illustrate the teachings of the present invention but in no way limit its scope as defined in the claims.

EXAMPLE 1

Ketal from Ethylene Glycol

A solution of δ-propionyl-p-chlorophenylacetonitrile(131 g.) more acturately defined as δ-propionyl-δ-(p-chlorphenyl)acetonitrile, ethylene glycol (70 g.), and p-toluenesulfonic acid (25 g.) in toluene (200 ml.) was heated at reflux in an apparatus fitted with a water separator. Vapor phase chromatographic (VPC) analysis indicated that the reaction was 96% complete after 2 hours. The reaction mixture was cooled and additional toluene (100 ml.) added. It was then washed with water (2×100 ml.), with 2% sodium hydroxide (1×100 ml.), and finally with water (3×100 ml.). The toluene was evaporated to give a thick oil (179 g.) which crystallized on standing. Recrystallization from methanol gave pure α-(p-chlorophenyl)-β-ethyl-β-ethylene-dioxypropionitrile, m.p. 58°–60°C. Elemental analysis: calcuiated for $C_{13}H_{14}NO_2Cl$: C, 62.03; H, 5.61; N, 5.57. Found: C, 62.60; H, 5.67; N, 5.88. Infrared and NMR analyses confirmed the structure.

EXAMPLES 2–7

Example 1 was repeated with the changes indicated. VPC analyses indicated the extent of reactions at the time shown

| Example | p-toluenesulfonic acid (g.) | ethylene glycol (g.) | Solvent | yield (%) | reaction time (hr.) |
|---|---|---|---|---|---|
| 2 | 8 | (1)* | (1) | 62 | 2 |
| 3 | 33 | (1) | (1) | 97 | 1¼ |
| 4 | (1) | 83 | (1) | 98 | 1½ |
| 5 | (1) | (1) | benzene (200 ml) | 93 | 4 |
| 6 | (1) | (1) | toluene (130 ml) | 90 | 1 |
| 7 | (1) | (1) | toluene (300 ml) | 85 | 1 |

*(1) indicates the conditions of Example 1.

EXAMPLE 8

Example 1 was repeated except that concentrated sulfuric acid was used instead of p-toluenesulfonic acid. VPC analysis indicated that the reaction was 25% complete after 1 hr.

EXAMPLE 9

An alcoholic solution of guanidine base, prepared by mixing guanidine hydrochloride (15 g.) in ethanol (50 ml.) with 25% sodium methylate in methanol (40 ml.) and filtering, was combined with α-(p-chlorophenyl)-β-ethyl-β-ethylenedioxypropionitril (28 g.). Methanol was removed by distillation until the pot temperature had reached 84°–86°C. The reaction mixture was then heated at reflux for 1 hr. and allowed to cool. The crystalline product was filtered and washed with ethanol, water, and acetone and then dried to give 22 g. (82%) of pyrimethamine, m.p. 238°–240°C. UV. and I.R. spectra were identical to those of an authentic sample.

EXAMPLE 10

Ketal from 1,2 Propylene Glycol

A solution of α-propionyl-p-chlorophenylacetonitrile (131 g.), 1,2-propanediol (85 g.), and p-toluenesulfonic acid (25 g.) in toluene (200 ml.) was heated at reflux in an apparatus fitted with a water separator. After 1½ hr. reflux the reaction was 97% complete by VPC analysis. The reaction mixture was cooled and washed (3×100 ml.) with 15% sodium chloride solution. The toluene was evaporated to give 189 g. of a thick oil.

Infrared analysis of the oil (A) as well as the starting α-propionyl-p-chlorophenylacetonitrile (B) showed the following:

| | Wave members, cm$^{-1}$ | | | |
|---|---|---|---|---|
| | —OH | —CN | >C=O | —C=C— |
| A | absent | 2240 | 1740 (trace) | absent |
| B | 3240 | 2250<br>2210 | 1735 | 1635 |

Example 11

Conversion of the Propylene Glycol Ketal to Pyrimethamine

An alcoholic solution of guanidine base, prepared by mixing guanidine hydrochloride (35.5 g.) in ethanol (100 ml.) with 25% sodium methylate in methanol (100 ml.) and filtering, was combined with the ketal (75 g.) from Example 10. Methanol was removed by distillation until the pot temperature had reached 85°–86°C. The reaction mixture was heated at reflux for 4 hr. and cooled overnight. The crystal product was filtered, washed with ethanol (30 ml.), water (30 ml.), 2% sodium hydroxide (40 ml), water (65 ml.), and finally ethanol (30 ml.). It was allowed to dry, giving pyrimethamine (36 g.), m.p. 238°–240°.

EXAMPLES 12–13

Examples 10 and 11 were repeated except that the propylene glycol was replaced by the indicated reactant on an equimolar basis and the ketal converted to pyrimethamine in the indicated yield based on starting ketonitrile.

| Example | Reactant | Yield (of Pyrimethamine) |
|---|---|---|
| 12 | 1,3-Propanediol | 78% |

-continued

| Example | Reactant | Yield (of Pyrimethamine) |
|---------|----------|--------------------------|
| 13 | Glycerol | 37% |

Dioxy (ketal) intermediate    Analysis Examples 12 & 13

| Example | Amount of Reactant | | | Diol (wt.) | Reflux Time (hr) | Ketal (g) | IR Analysis (wave members, cm$^{-1}$) | | | | Pyrimethamine (% yield) |
| | A (g) | B (g) | C (ml) | | | | OH | CN | CO | C=C | |
|---|---|---|---|---|---|---|---|---|---|---|---|
| 16 | 21 | 4 | 50 | D (20) | 2 | 32 | absent | 2240 | 1735 (trace) | absent | 72 |
| 17 | 41.5 | 8 | 100 | E (36) | 1.5 | 57 | * | | | | 20 |
| 18 | 66 | 12.5 | 100 | F (51) | 3 | 100 | absent | 2245 | 1735 (trace) | absent | 68 |
| 19 | 30.5 | 6 | 50 | G (31) | 2 | 35 | absent | 2240 | 1735 (trace) | absent | 79 |
| 20 | 66 | 12 | 100 | H (66) | 2 | 80 | trace | 2200 2240 | 1735 (trace) | trace | 59 |

*The intermediate of Example No. 17 was not examined by infrared.

| | mp | IR Analysis (wave members, cm$^{-1}$) |
|---|---|---|
| 12 | 102–103° C. | CN, 2242; OH, CO, C=C absent |
| 13 | oil | OH, 3480; CN, 2242; CO, 1740 (trace); C=C absent |

EXAMPLE 14

Effect of Scale-Up

Example 1 was repeated at various degrees of scale-up and the conversion to ketal determined by VPC.

| Scale (moles of keto nitrile) | Conversion (%) |
|---|---|
| 0.6 | 95–100 |
| 5.0 | 95–98 |
| 200. | 94–96 |

EXAMPLE 15

Comparison with Enol Ether

Example 1 was repeated with two exceptions, (1) n-amyl alcohol was used in place of ethylene glycol to give the enol ether, α-(p-chlorophenyl)-β-ethyl-β-(n-amyloxy) acrylonitrile and (2) the reaction was carried out at various degrees of scale-up.

| Scale (moles of keto nitrile) | Conversion (%) |
|---|---|
| 0.5 | 95–100 |
| 200. | 85 |
| 2000. | 70 |

In Examples 16–20 a reaction mixture comprising a diol, α-propionyl-p-chlorophenylacetonitrile (A), p-toluenesulfonic acid (B) and toluene (C) was heated at reflux for the time indicated in an apparatus fitted with a water separator. The reaction mixture was then cooled to room temperature and additional toluene (100 ml) added. It was then thoroughly washed with water and the toluene evaporated. The resulting ketal, an oil in each case, was analyzed by infrared spectroscopy. The oil was then converted to 2,4-diamino-6-ethyl-5-(p-chlorpheyl)pyrimidine (pyrimethamine) according to the general procedure of Example 9. The yield given is for the two steps from diol to pyrimethamine. Diols used were 3-methoxy-1,2-propanediol (D), 1,4-butanediol (E), 2,3-butanediol (F), 3-chloro-1,2-propanediol (G), and 1,2-cyclohexanediol (mixture of cis and trans) (H). α-Propionyl-p-chlorophenylacetonitrile exhibits the following peaks in the infrared: OH at 3240 cm$^{-1}$, CN at 2210 and 2250 cm$^{-1}$, C=O at 1735 cm$^{-1}$ and C=C at 1635 cm$^{-1}$.

We claim:
1. A compound of the formula

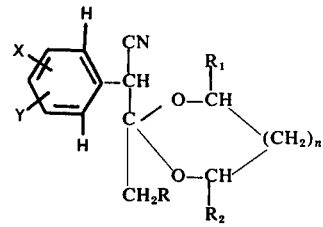

where $n = 0$, 1 or 2, R is alkyl of 1 to 10 carbon atoms or a hydrogen atom, $R_1$ and $R_2$ are the same or different and each is a hydrogen atom or lower alkyl of 1 to 4 carbon atoms optionally substituted with hydroxy, lower alkoxy or a halogen atom, X is a halogen atom or nitro, Y is a halogen atom or a hydrogen atom, or $R_1$ and $R_2$ taken together can complete a 5 to 7 member saturated ring when $n = 0$.

2. The compound of claim 1 which is

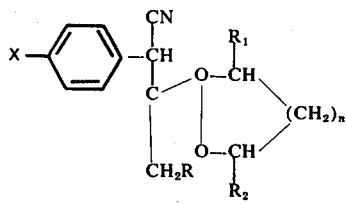

where X, R, $R_1$ and $R_2$ and $n$ are as defined in claim 1.

3. The compound of claim 2 in which X is a chlorine atom and R is methyl.

4. The compound of claim 3 in which $n = 0$ and $R_1$ and $R_2$ are hydrogen.

5. The compound of claim 3 in which $n = 1$ and $R_1$ and $R_2$ are hydrogen.

6. The compound of claim 3 in which $n = 0$ and $R_1$ is methyl and $R_2$ is hydrogen.

7. The compound of claim 1 in which R is lower alkyl of 1 to 4 carbon atoms.

8. The compound of claim 2 in which R is lower alkyl of 1 to 4 carbon atoms.

9. The compound of claim 2 in which X is a chlorine atom and R is lower alkyl of 1 to 4 carbon atoms or a hydrogen atom.

10. The compound of claim 9 in which $R_1$ and $R_2$ are the same or different and each is lower alkyl of 1 to 4 carbon atoms or a hydrogen atom.

11. The compound of claim 1 in which $n = 0$, $R_2$ is hydrogen and $R_1$ is $CH_2Z$ where Z is a chlorine atom or methoxyl.

12. The compound of claim 3 in which $R_1$ and $R_2$ are the same or different and each is lower alkyl of 1 to 4 carbon atoms or a hydrogen atom.

13. The compound of claim 12 where $n$ is 0 or 1.

14. The compound of claim 1 wherein $n$ is 0 or 1.

15. The compound of claim 2 where $n$ is 0 or 1.

16. The compound of claim 3 wherein $n$ is 0 or 1.

17. The compound of claim 14 where R is lower alkyl of 1 to 4 carbon atoms.

18. The compound of claim 15 where R is lower alkyl of 1 to 4 carbon atoms.

* * * * *